US00PP34459P2

(12) United States Plant Patent
O'Connell

(10) Patent No.: US PP34,459 P2
(45) Date of Patent: Jul. 26, 2022

(54) ***SEDUM* PLANT NAMED 'SUNSTAR'**

(50) Latin Name: *Sedum adolphi*
Varietal Denomination: 'SUNSTAR'

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/577,665

(22) Filed: Jan. 18, 2022

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Sedum* plant named 'Sunstar' is disclosed, characterized by golden orange foliage accentuated by deep vermillion leaf tips and margins. Plants are diminutive with robust growth, useful for decorative centerpieces and dish gardens. The robust growth of the new variety enhances production times in the commercial nursery. The new variety is a *Sedum*, typically be produced as a container plant for the patio or as landscape plants, as well as a variety of ornamental purposes.

2 Drawing Sheets

Figure 1:
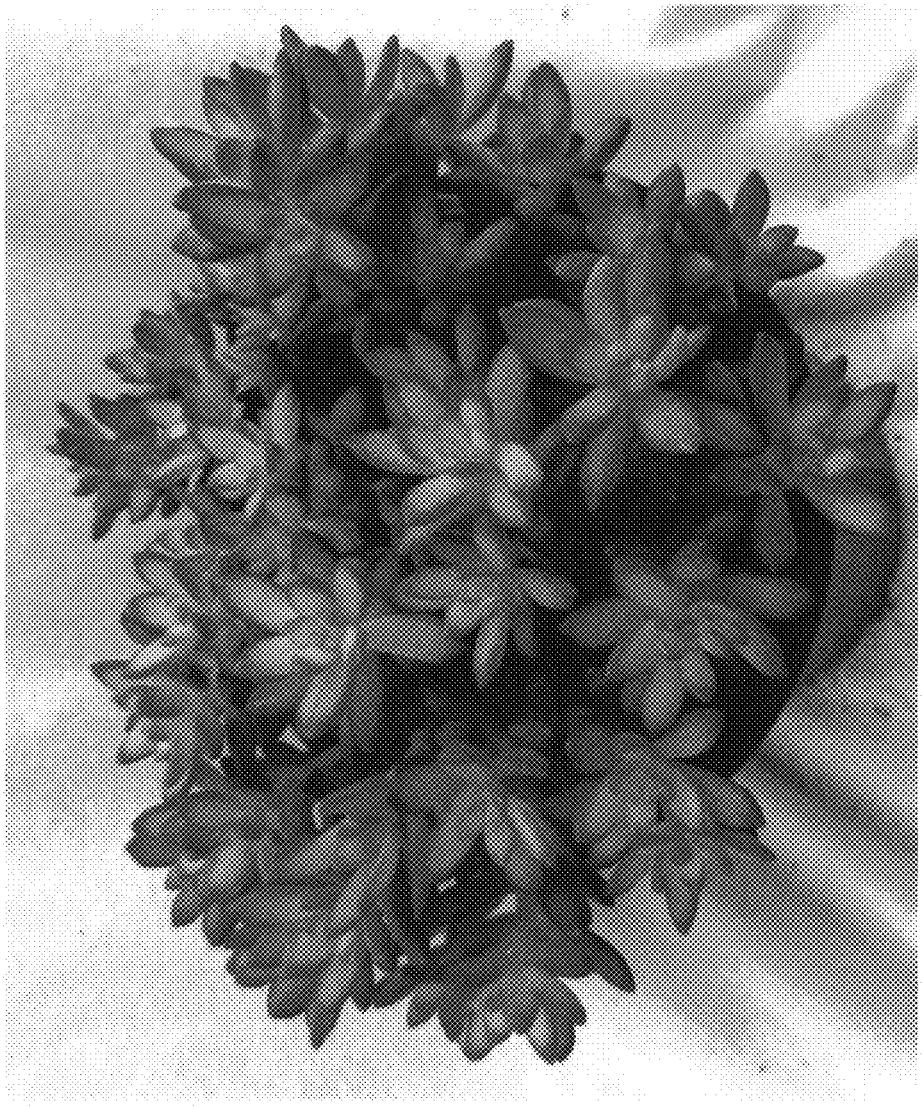

Latin name of the genus and species: *Sedum adolphi.*
Variety denomination: 'SUNSTAR'.

BACKGROUND OF THE INVENTION

The new cultivar, *Sedum* 'SUNSTAR', is the product of chance discovery. The new variety originated as a naturally occurring whole plant mutation of the parent, an unnamed *Sedum adolphi* (unpatented). The new cultivar 'SUNSTAR' was discovered by the inventor, Renee O'Connell, in May of 2018, in Vista, Calif., at a commercial greenhouse.

Asexual reproduction of the new cultivar 'SUNSTAR' was first performed June 2018 in Vista, Calif., at a commercial greenhouse, by terminal vegetative cuttings. *Sedum* 'SUNSTAR' has since produced multiple generations and has shown that the unique features of this cultivar are stable and reproduced true to type.

SUMMARY OF THE INVENTION

The cultivar 'SUNSTAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUNSTAR'. These characteristics in combination distinguish 'SUNSTAR' as a new and distinct *Sedum* cultivar:

1. The new cultivar *Sedum adolphi* 'SunStar' forms multiheaded clusters of golden orange leaves, accentuated by deep vermillion leaf tips and margins.
2. *Sedum adolphi* 'SunStar', due to its diminutive, brightly colored form is ideal for use in decorative centerpieces and mixed plantings of succulents known as dish gardens.

3. *Sedum adolphi* 'SunStar', although diminutive, shows the same robust growth of the type species *Sedum adolphi.*
4. *Sedum adolphi* 'SunStar' branches profusely, enhancing propagation numbers in a commercial nursery.
5. *Sedum adolphi* 'SunStar' is fast-growing, enhancing production times in a commercial nursery.

PARENTAL COMPARISON

Plants of the new cultivar are similar to plants of the parent, in most horticultural characteristics, however, plants of the new cultivar differ in the following;

1. *Sedum adolphi* 'Sunstar' forms plants that are much smaller than the parent. Stem rosettes of the new variety are approximately 20% of the size of those of the parent variety.
2. *Sedum adolphi* 'SunStar', branches more profusely than the parent, enhancing propagation numbers in a commercial nursery.
3. *Sedum adolphi* 'Sunstar' produces brighter colored leaves with brighter vermillion tips than those of the parent.

COMMERCIAL COMPARISON

The new cultivar 'Sunstar' can be compared to the unpatented commercial variety *Sedum adolphi* 'Firestorm', found in horticultural commerce. Plants of *Sedum* 'Firestorm' are similar to plants of the new cultivar 'Sunstar' in most horticultural characteristics. However, the new cultivar 'Sunstar' differs in the following:

1. *Sedum adolphi* 'SunStar' forms multiheaded clusters of golden orange leaves with bright vermillion leaf tips and margins, whereas *Sedum adolphi* 'Firestorm' forms multiheaded clusters of orange vermillion leaves, with a darker margin.

2. *Sedum adolphi* 'SunStar' exhibits shorter, wider leaves than does *Sedum adolphi* 'Firestorm', which has longer, more slender leaves.
3. *Sedum adolphi* 'SunStar' produces leaves of golden orange, with vermillion tips and margins, creating a colorful contrast of colors. *Sedum adolphi* 'Firestorm' displays leaves of orange vermillion, displaying less contrast between the two colors.
4. *Sedum adolphi* 'SunStar', exhibits a more compact growth than does *Sedum adolphi* 'Firestorm', which quickly begins displaying a rambling growth.

The new cultivar 'Sunstar' can be compared to the unpatented commercial variety *Sedum* 'Sunset'. Plants of *Sedum* 'Sunset' are similar to plants of the new cultivar 'Sunstar' in most horticultural characteristics. However, plants of the new cultivar 'Sunstar' differ in the following:

1. *Sedum adolphi* 'SunStar' exhibits a much more diminutive morphology than does *Sedum adolphi* 'Sunset'.
2. *Sedum adolphi* 'SunStar' produces leaves of golden orange, with vermillion tips and margins, creating a colorful contrast of colors. *Sedum adolphi* 'Sunset' displays leaves of orange vermillion, displaying less contrast between the two colors.
3. *Sedum adolphi* 'SunStar', exhibits shorter, wider leaves, as compared with the longer, more slender leaves of *Sedum adolphi* 'Sunset'.

BRIEF DESCRIPTION OF THE PHOTOGRAPHS

The accompanying photograph in FIG. 1 illustrates in full color a typical plant of 'SUNSTAR' grown in a greenhouse in Vista, Calif. (approximately 3000 to 3500 foot candles) at approximately 6 months of age from a rooted cutting.

Figure 2:
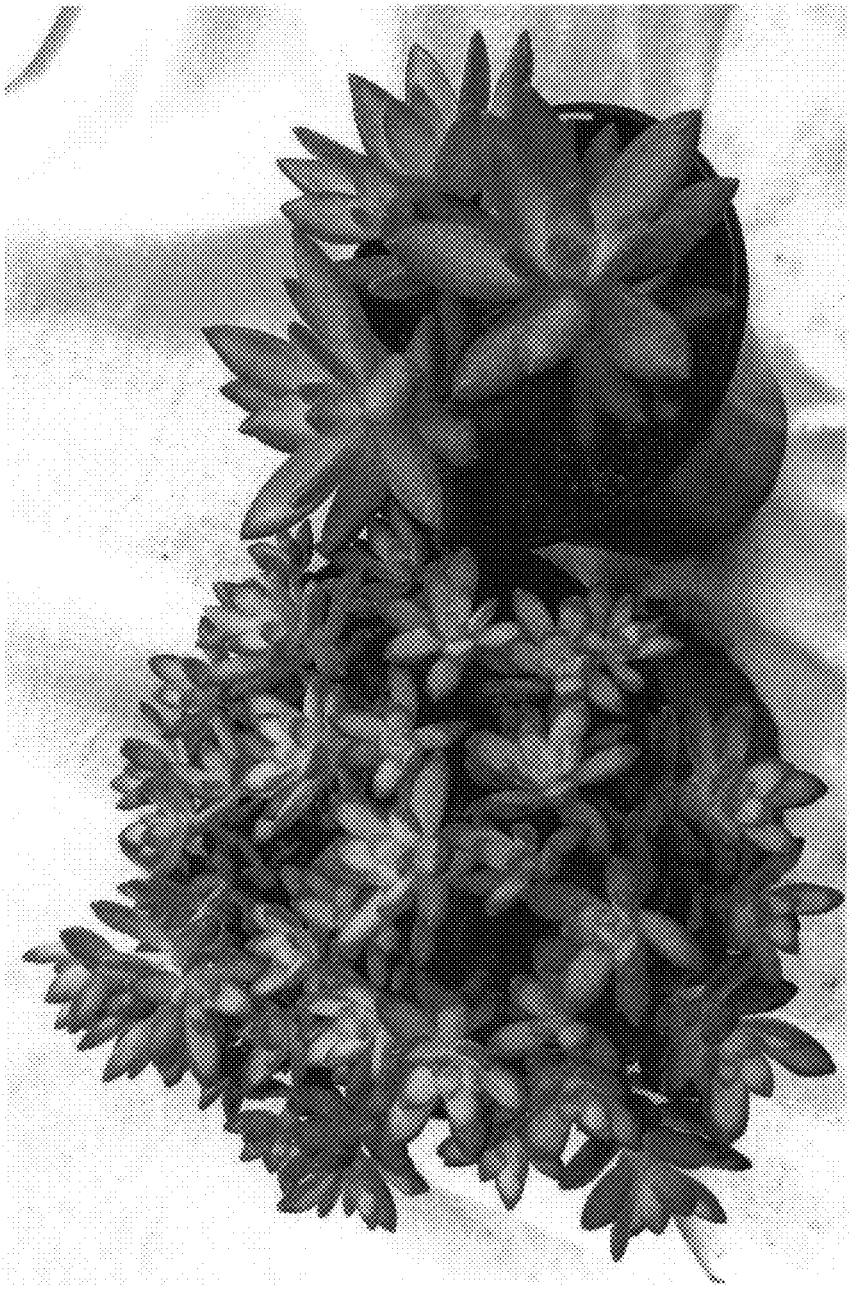

FIG. 2 illustrates a plant of the new variety 'Sunstar' on the left with a plant of the parent plant on the right.

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Sedum* plant. Temperatures ranged from 2° C. to 29° C. night and day. No artificial light, photoperiodic treatments or chemical treatments were given to the plants.

DETAILED BOTANICAL DESCRIPTION

In the following description, color references are made to The Royal Horticultural Society Colour Chart, 2007 except where general terms of ordinary dictionary significance are used. The following observations and measurements describe 'Sunstar' plants in a commercial greenhouse in Vista, Calif. Temperatures ranged from about 1° C., to 35° C. night and day. No artificial light, photoperiodic treatments or chemical treatments were given to the plants. Natural light conditions were approximately 2500 fc of light. Measurements and numerical values represent averages of typical plant types.

Botanical classification: *Sedum adolphi* 'SUNSTAR'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 1 gallon.

Growth habit: Semi-upright succulent, mounding then semi-trailing.

Height: Approximately 12 to 14 cm.

Plant spread: Approximately 20 cm.

Vigor: Robust, fast growing.

Branching characteristics: Basal occurring main branches. Abundant sub-opposite lateral branches.

*Length*.—Main branches about 10 cm, lateral branches about 5 cm to 8 cm.

*Width*.—5 to 6 mm.

*Color*.—Near Yellow-Green 145C. Flushed Greyed-Red 182C with maturity.

*Texture*.—Glabrous.

*Appearance*.—Matte.

*Strength*.—Moderately strong.

*Internode*.—About 15 mm.

Foliage:

*Arrangement*.—Sub-opposite, forming very dense, evenly spaced rosettes.

*Foliar internode*.—About 2 mm.

*Average length*.—Mature foliage average range 2.5 cm to 2.8 cm.

*Average width*.—10 mm.

*Width at base*.—5 mm.

*Center (deepest) depth*.—5 mm.

*Shape of blade*.—Oblong.

*Apex*.—Acute.

*Base*.—Truncate.

*Margin*.—Entire.

*Texture of top surface*.—Glabrous.

*Texture of bottom surface*.—Glabrous.

*Appearance of top surface*.—Shiny.

*Appearance of top surface*.—Shiny.

*Quantity*.—Average of 50 on one main branch ending in 3 rosettes.

*Color*.—Young foliage upper side: Near Yellow-Green 145B, base near 145C. Strong marginal coloration near Greyed-Purple 183B, uppermost margin Greyed-Purple 187B. Young foliage under side: Near Yellow-Green 145B, base near 145C. Strong marginal coloration near Greyed-Purple 183B, uppermost margin Greyed-Purple 187B. Mature foliage upper side: Near Yellow-Green 145B, base near 145C. Strong marginal coloration near Greyed-Purple 183B, uppermost margin Greyed-Purple 187B. Mature foliage under side: Near Yellow-Green 145B, base near 145C. Strong marginal coloration near Greyed-Purple 183B, uppermost margin Greyed-Purple 187B.

*Venation*.—Indistinguishable from leaf blade.

Flower: Not observed.
Reproductive organs: Not observed.
Other characteristics:

*Fruits and seeds*.—Not observed.

*Temperature tolerance*.—Tolerates temperatures from approximately 0° C. to at least 32° C.

*Disease/pest resistance*.—Neither resistance or susceptibility to other normal diseases and pests of *Sedum* has been observed.

*Drought tolerance*.—Tolerates at least 2 weeks of high temperatures without supplemental water, showing no serious damage to plant.

What is claimed is:

1. A new and distinct cultivar of *Sedum* plant named 'SUNSTAR' as herein illustrated and described.

* * * * *